(12) United States Patent
Mueller et al.

(10) Patent No.: US 7,119,082 B2
(45) Date of Patent: *Oct. 10, 2006

(54) 11β-LONG-CHAIN-SUBSTITUTED 19-NOR-17α-PREGNA-1,3,5(10)-TRIEN-17β-OLS WITH A 21,16α-LACTONE RING

(75) Inventors: Gerd Mueller, Jena (DE); Jens Hoffmann, Muehlenbeck (DE); Karl-Heinrich Fritzemeier, Berlin (DE); Alexander Hillisch, Jena (DE)

(73) Assignee: Schering Aktiengesellschaft, Berlin (DE)

( * ) Notice: Subject to any disclaimer, the term of this patent is extended or adjusted under 35 U.S.C. 154(b) by 174 days.

This patent is subject to a terminal disclaimer.

(21) Appl. No.: 10/397,854

(22) Filed: Mar. 27, 2003

(65) Prior Publication Data

US 2003/0229059 A1 Dec. 11, 2003

Related U.S. Application Data

(60) Provisional application No. 60/374,516, filed on Apr. 23, 2002.

(30) Foreign Application Priority Data

Mar. 27, 2002 (DE) ................................. 102 14 180

(51) Int. Cl.
*A61K 31/58* (2006.01)
*C07J 71/00* (2006.01)
(52) U.S. Cl. ........................................ 514/174; 540/65
(58) Field of Classification Search .................. 540/65; 514/174
See application file for complete search history.

(56) References Cited

U.S. PATENT DOCUMENTS 6,670,347 B1 * 12/2003 Muller et al. ................ 514/175

* cited by examiner

*Primary Examiner*—Barbara P. Badio
(74) *Attorney, Agent, or Firm*—Millen, White, Zelano & Branigan, P.C.

(57) ABSTRACT

This invention relates to new 19-nor-17α-pregna-1,3,5(10)-trien-17β-ols with a 21,16α-lactone ring with a long-chain substituent in 11β-position of general formula II

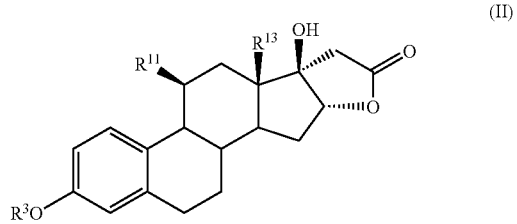

(II)

in which $R^{11}$ means a straight-chain alkyl radical with 6 to 17 carbon atoms, and $R^3$ and $R^{13}$ have the meanings that are explained in more detail in the description. The compounds act in a tissue-selective manner as pure antiestrogens and are suitable for the production of pharmaceutical agents because of these properties.

20 Claims, 1 Drawing Sheet

11β-LONG-CHAIN-SUBSTITUTED 19-NOR-17α-PREGNA-1,3,5(10)-TRIEN-17β-OLS WITH A 21,16α-LACTONE RING

This application claims the benefit of the filing date of U.S. Provisional Application Ser. No. 60/374,516, filed Apr. 23, 2002.

This invention relates to new 11β-long-chain-substituted 19-nor-17α-pregna-1,3,5(10)-trien-17β-ols with a 21,16α-lactone ring, process for their production and pharmaceutical preparations that contain these compounds as well as the use of these compounds for the production of pharmaceutical agents.

Estrogens exert their physiological action on receptor proteins, the estrogen receptors (ERs). In this case, these are nuclear-position transcription factors that can be activated by ligands. Until a few years ago, it was assumed that estrogens exert their action via a single receptor.

Only since 1996 has it become known that two subtypes of the estrogen receptor exist (ERα and ERβ) (Kuiper et al., Proc. Natl. Acad. Sci. USA 93, 1996, 5925–5930). Both are distinguished in their expression pattern in different tissues. Thus, for example, ERβ predominates over ERα in the rat prostates, while ERα predominates in the rat uterus. Areas were identified in the brain in which in each case only one of the two ER subtypes is expressed (Shugrue et al., Steroids 61, 1996, 678–681; Li et al., Neuroendocrinology 66, 1997, 63–67). Both ERα and ERβ are expressed in bones (Kuiper et al., Frontiers in Neuroendocrinology 1998, 19: 253–286), blood vessels (Iafrati et al., Nature Med. 1997, 3: 545–48) and normal breast tissue (Gustafsson and Warner, J. Steroid Biochem. Mol. Biol. 74, 2000, 245–248).

In malignant, degenerated breast tissue, an up-regulation of ERα expression as well as a reduced ERβ expression were observed in several independent works (Leygue et al., Cancer Res. 58, 1998, 3197–3201; Iwao et al., Int. J. Cancer 88, 2000, 733–736; Lacennec et al., Endocrinology 142, 2001, 4120–4130; Roger et al., Cancer Res. 61, 2001, 2537–2541). ERβ knock-out mice (deficient ERβ) exhibit an abnormal epithelial growth of the breast and an over-expression of proliferation marker Ki67 (Gustafsson and Warner, 2000). Also, an inverse correlation between ERβ expression and Ki67 was detected in humans (Roger et al., 2001). In addition, ERβ acts as an inhibitor of ERα transcriptional activity and lowers the cellular sensitivity to estradiol (Hall and McDonnell, Endocrinology 140, 1999, 5566–5578). These data support the hypothesis that ERβ, i.a., shows a protective factor against the mitogenic activity of estrogens that is mediated by ERα. ERβ can therefore be regarded as an endogenic antagonist of ERα.

In patents by Katzenellenbogen et al. (WO 00/19994) and Loozen et al. (WO 00/31112), subtype-specific estrogen receptor ligands, i.a., ERα-selective compounds, are described.

WO 01/00652 discloses 11β-long-chain-substituted estratrienes of general formula I,

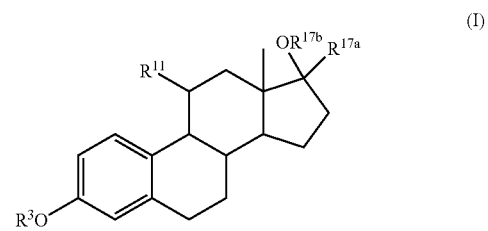

in which R11 is a long-chain radical that has a nitrogen atom as well as optionally a sulfur atom, which in addition can be functionalized in terminal position with a perfluoroalkyl group or an optionally substituted aryl radical. The compounds have at their disposal antiestrogenic or tissue-selective estrogenic properties and are suitable for the production of pharmaceutical agents.

In the un-prepublished application DE 100 48 634, 19-nor-17α-pregna-1,3,5(10)-trien-17β-ols with a 21,16α-lactone ring are described as selective estrogens, which show preference for estrogen receptor α in contrast to standard estrogens such as estradiol.

The object of this invention consists in making available new compounds that have in vitro a dissociation with respect to their binding to estrogen receptor preparations of rat prostates and rat uteri and in vivo an antiproliferative action via the preferential antagonizing of ERα, without preventing the positive properties of the ERβ. This also includes a preferential suppression of the expression of ERα without reduction of the ERβ expression.

The object is [achieved] according to this invention by the preparation of novel 19-nor-17α-pregna-1,3,5(10)-trien-17β-ols with a 21,16α-lactone ring with a long-chain substituent in 11β-position of general formula II

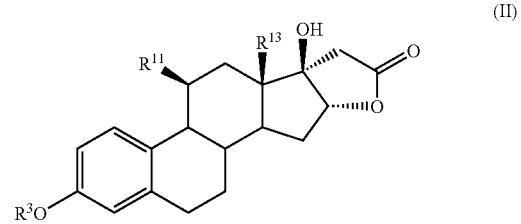

in which

R$^3$ represents a hydrogen atom, a C$_{1-4}$-alkyl, C$_{2-6}$-acyl or tri(C$_{1-4}$-alkyl)silyl group or a group R$^{18}$SO$_2$—, whereby R$^{18}$ represents a group R$^{19}$R$^{20}$N—, in which R$^{19}$ and R$^{20}$, independently of one another, are a hydrogen atom, a C$_{1-5}$-alkyl radical, a group C(O) R$^{21}$ and in which R$^{21}$ represents a straight-chain or branched hydrocarbon radical with up to 6 carbon atoms, a C$_{3-7}$- cycloalkyl radical, an aryl radical, which optionally can be substituted, an aralkyl radical or an alkylaryl radical, and $R^{11}$ means a straight-chain alkyl radical with 6 to 17 carbon atoms, and $R^{13}$ means a methyl or ethyl group.

Another subject of this invention relates to pharmaceutical agents that contain a compound of general formula II or their pharmaceutically acceptable addition salts with organic or inorganic acids.

Unless defined in more detail otherwise in terms of this invention, this is an aryl radical that optionally can be substituted by a phenyl, 1- or 2-naphthyl radical, whereby the phenyl radical is preferred. Unless expressly indicated otherwise, aryl always also includes a heteroaryl radical. Examples of a heteroaryl radical are the 2-, 3- or 4-pyridinyl radical, the 2- or 3-furyl radical, the 2- or 3-thienyl radical, the 2- or 3-pyrrolyl radical, the 2-, 4- or 5-imidazolyl radical, the pyrazinyl radical, the 2-, 4- or 5-pyrimidinyl radical or the 3- or 4-pyridazinyl radical.

As substituents for an aryl or heteroaryl radical, for example, a methyl, ethyl, trifluoromethyl, pentafluoroethyl, trifluoromethylthio, methoxy, ethoxy, nitro, cyano, halogen (fluorine, chlorine, bromine, iodine), hydroxy, amino, mono ($C_{1-8}$-alkyl) or di($C_{1-8}$-alkyl)amino, whereby both alkyl groups are identical or different, and di(aralkylamino), whereby both aralkyl groups are identical or different, can be mentioned.

For substituent $R^{11}$, for example, hexyl, heptyl, decyl, and dodecyl can be mentioned as representatives of straight-chain alkyl chains with 6 to 17 carbon atoms.

As representatives of alkyl radicals or straight-chain or branched-chain alkyl groups with up to 12 carbon atoms in terms of $R^3$, $R^{19}$ and $R^{20}$ or $R^{21}$, for example, methyl, ethyl, propyl, isopropyl, butyl, isobutyl, tert-butyl, pentyl, isopentyl, neopentyl, hexyl, heptyl, and decyl can be mentioned. Methyl, ethyl, propyl and isopropyl are preferred.

$C_{2-6}$-acyl radicals mean, for example, acetyl, propionyl, butyryl, valeroyl, isovaleroyl, pivaloyl, and hexanoyl.

Representatives of the above-mentioned $C_{3-7}$-cycloalkyl group can be, for example, cyclopropyl, cyclobutyl, cyclopentyl, or cyclohexyl.

The hydroxyl group at C-atom 3 can be esterified with an aliphatic, straight-chain or branched-chain, saturated or unsaturated $C_{2-6}$-carboxylic acid. As such carboxylic acids for esterification, the following are considered, for example: acetic acid, propionic acid, butyric acid, isobutyric acid, valeric acid, isovaleric acid or pivalic acid.

As examples of a tri($C_{1-4}$-alkyl) group, a trimethylsilyl group and a tert-butyldimethyl group can be mentioned.

According to the invention, compounds of general formula II

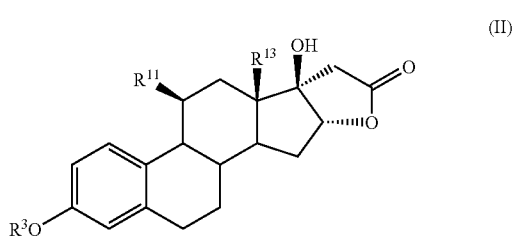

(II)

are preferred, in which $R^3$ means a hydrogen atom or a methyl group and $R^{13}$ means a methyl group, and $R^{11}$ can be selected from the group of the following side chains: hexyl, octyl, decyl and dodecyl.

Especially preferred 11β-long-chain-substituted 19-nor-17α-pregna-1,3,5(10)-trienes with a 21,16α-lactone ring are, for example:

3,17β-Dihydroxy-11β-hexyl-19-nor-17α-pregna-1,3,5 (10)-triene-21,16α-lactone 3,17β-dihydroxy-11βoctyl-19-nor-17α-pregna-1,3,5(10)-triene-21,16α-lactone 3,17β-dihydroxy-11β-decyl-19-nor-17α-pregna-1,3,5 (10)-triene-21,16α-lactone 3,17β-dihydroxy-11β-dodecyl-19-nor-17α-pregna-1,3,5 (10)-triene-21,16α-lactone For the formation of pharmaceutically compatible salts of the compounds of general formula II according to the invention, i.a., hydrochloric acid, hydrobromic acid, sulfuric acid and phosphoric acid are suitable as inorganic acids, and, i.a., acetic acid, propionic acid, maleic acid, fumaric acid, succinic acid, benzoic acid, ascorbic acid, oxalic acid, salicylic acid, tartaric acid, citric acid, lactic acid, malic acid, mandelic acid, cinnamic acid and methanesulfonic acid are suitable as organic acids.

The substances of general formula II according to the invention represent compounds that are distinguished by a new structural element, a 21,16α-lactone ring, compared to the compounds with long-chain 11β-side chains that are known from the prior art. It was found that 11β-substituted 19-nor-17α-pregna-1,3,5(10)-trien-17β-ols with a 21,16α-lactone ring according to the invention selectively show, in a surprising way, an antagonistic action on the ERα. With the substances according to the invention, it is possible preferably to antagonize the ERα without preventing the positive properties of the ERβ. This also includes a preferential suppression of the expression of ERα without reduction of the ERβ expression.

Biological Characterization of the Compounds According to the Invention

The substances of general formula II according to the invention were tested in various models. Via the selective inhibition of the ERα, the substances according to the invention exert an antiproliferative action in other hormone-modulated tumors in addition to the breast tissue.

Estrogen Receptor Binding Studies

Methodology

The binding affinity of the new selective antiestrogens was tested in competitive experiments with use of 3H-estradiol as a ligand on estrogen receptor preparations of rat prostates and rat uteri. The preparation of the prostate cytosol and the estrogen receptor test with prostate cytosol was performed as described in the literature (Testas et al., Endocrinology 109, 1981, 1287–1289).

The preparation of rat uterus cytosol as well as the receptor test with the estrogen-receptor-containing cytosol was performed in principle according to Stack and Gorski (Stack, Gorski, Endocrinology 117, 1985, 2024–2032) with several modifications (Fuhrmann et al., Contraception 51, 1995, 45–52).

The substances according to the invention, such as, for example 3,17β-dihydroxy-11β-hexyl-19-nor-17α-pregna-1, 3,5(10)-triene-21,16α-lactone (compound 1), have a higher binding affinity to the estrogen receptor from the rat uterus than to the estrogen receptor from the rat prostate (see Table 1).

TABLE 1

| Compound | Structure | Rat Uterus ER (RBA) | Rat Prostate ER (RBA) | Uterus-ER/ Prostate-ER |
|---|---|---|---|---|
| Estradiol | 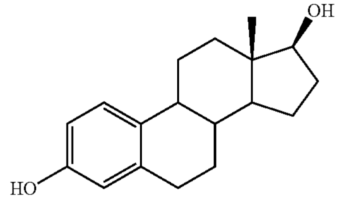 | 100 | 100 | 1 |
| Compound 1 | 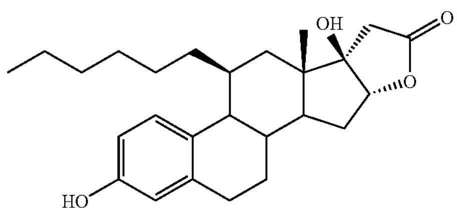 | 26.2 | 1.2 | 22 |

Compound 1: 3,17β-Dihydroxy-11β-hexyl-19-nor-17α-pregna-1,3,5(10)-triene-21,16α-lactone
RBA: Relative binding affinity
ER: Estrogen receptor In this case, it is assumed that ERβ predominates in the rat prostate over ERα, and ERα predominates in the rat uterus over ERβ. Table 2 shows that the ratio of binding to prostate and uterus receptors corresponds qualitatively to the quotient of the relative binding affinity (RBA) to human ERβ and rat ERα (Kuiper et al., Endocrinology 138, 1996, 863–870).

TABLE 2

| Estrogen | Struktur | hER α RBA* | hER β RBA* | ERβ/ ERα | Rat uterus ER(RBA) | Rat prost. ER(RBA) | Uterus-ER/ Prostata-ER |
|---|---|---|---|---|---|---|---|
| Estrodiol | | 100 | 100 | 1 | 100 | 100 | 1 |
| Estron | | 60 | 37 | 0.6 | 3 | 2 | 0.8 |
| 17α-Estrodiol | | 58 | 11 | 0.2 | 2.4 | 1.3 | 0.5 |

TABLE 2-continued

| Estrogen | Struktur | hER α RBA* | hER β RBA* | ERβ/ ERα | Rat uterus ER(RBA) | Rat prost. ER(RBA) | Uterus-ER/ Prostata-ER |
|---|---|---|---|---|---|---|---|
| Estriol | 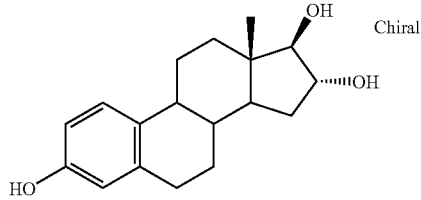 | 14 | 21 | 1.5 | 4 | 20 | 5 |
| 5-Androstendiol | 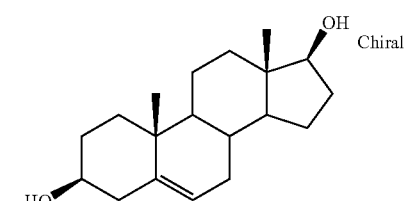 | 6 | 17 | 3 | 0.1 | 5 | 50 |
| Genistein | 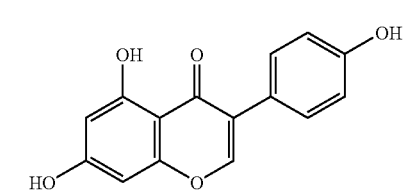 | 5 | 36 | 7 | 0.1 | 10 | 100 |
| Coumestrol | 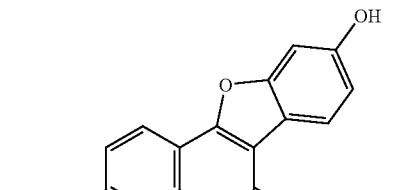 | 94 | 185 | 2 | 1.3 | 24 | 18 |

*zitiert aus: Kuiper et al. (1996), Endocrinology 138: 863–870
hER: humaner Estrogenrezeptor

[Key to Table 2:]
Struktur=Structure
Prostata=Prostate
Estron=Estrone
Androstendiol=Androstenediol
Genistein=Genisteine
*cited from: Kuiper et al. (1996), Endocrinology 138: 863–870
hER: human estrogen receptor Cell Proliferation Assay Breast cancer cell line MCF-7 is a hormone-dependent human cell line. The growth of these ER-positive cells is stimulated by estradiol and can be antagonized with partial-agonistic and pure antiestrogens (Lippmann et al. 1976, Wakelin et al. 1991). The substances according to the invention, for example 3,17β-dihydroxy-11β-hexyl-19-nor-17α-pregna-1,3,5(10)-triene-21,16α-lactone (compound 1), exert an antiproliferative action on the estradiol-modulated tumors via the selective inhibition of the ERα.

Material and Methods

The readily characterized breast cancer cell line MCF-7 was established from the pleural exudate of a 69-year-old patient with disseminated breast cancer (Soule et al. 1973). The cells are cultivated in RPMI medium 1640 without phenol red, 1% L-glutamine, 200 mmol of insulin/ml and 10% FCS or CCS in an incubator at 37° C. and water vapor-saturated atmosphere with 5% $CO_2$.

The medium is changed every three to four days. Cells that grow confluently in the cell culture flask to 80–90% are passaged.

In the tests, the test substances were checked for their estradiol-stimulated proliferation-inhibiting properties.

For the tests, the dissemination of a defined cell number in a 96-hole plate is carried out in 200 μl medium/hole (5000 cells/hole). Two columns are filled only with medium as blanks. 24 hours later, after adhesion of the cells has been completed, the medium is varied by adding the substances to be tested. The test substances, dissolved as stock solution in absolute ethanol (EtOH), are added at increasing concentrations. In addition to a solvent control, an estradiol control is also used. The test period is 7 days, within which the medium is changed after three days. The proliferation is determined with the crystal violet assay. This method is based on the staining of DNA in the nucleus by crystal violet (N-hexamethylpararosaniline) (Wakelin et al. 1981). The intensity of the blue staining, which depends on the amount of crystal violet that is bonded to the DNA, can be quantified by spectral-photometric measurements. The extinction values correspond to the amount of DNA and thus the number of cell nuclei. They are equated as indirect parameters of the cell number (Gillies et al. 1986).

The cells are fixed at the end of the test with 25 μl of glutardialdehyde solution (11%) per hole for 20 minutes at room temperature by a slight shaking. The perforated disk is rapped to remove excess material, washed under running, demineralized water (VE-water) and air-dried. After 100 μl of crystal violet (0.1%, pH 4.5) is added per hole to the fixed cells, it is shaken for 20 minutes at room temperature. After being washed and air-dried again, 100 μl of acetic acid (10%) is added per hole, shaken briefly, and the extinction at 595 nm is measured in a spectral photometer (Kueng et al. 1989).

Results

As can be seen in FIG. 1, 3,17β-dihydroxy-11β-hexyl-19-nor-17α-pregna- 1,3,5(10)-triene-21,16α-lactone (compound 1) inhibits the growth of MCF-7 breast cancer cells. A dose-action relationship exists. At a concentration of $10^{-5}$ M, the estradiol-stimulated proliferation of the MCF-7 breast cancer cells is inhibited to 100%.

Figure 1:
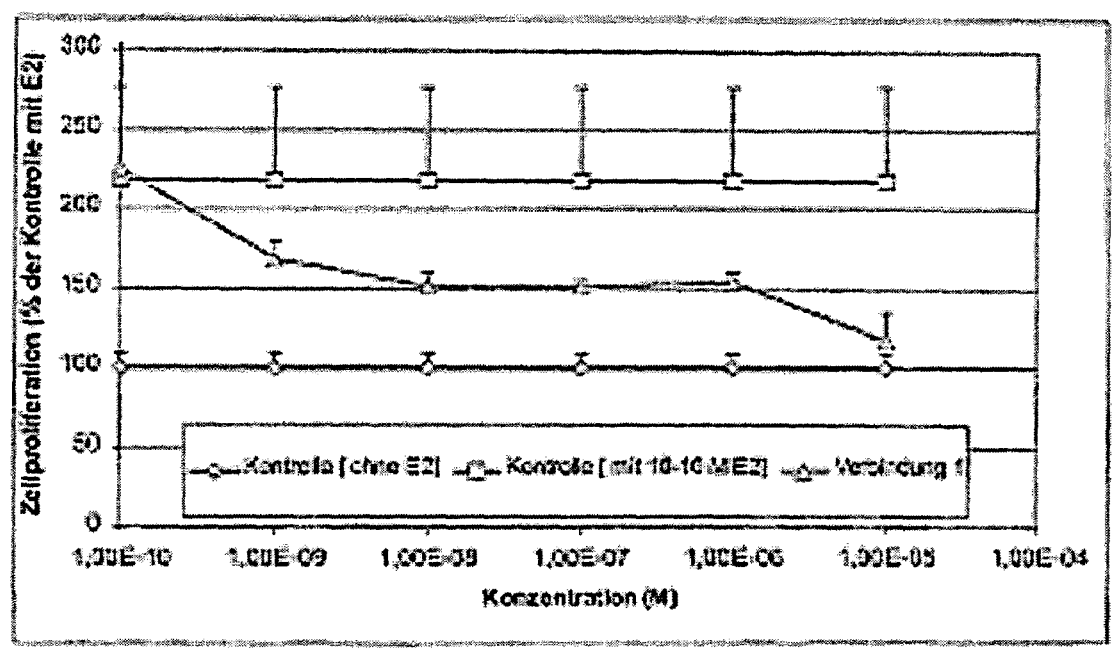
FIG. 1 illustrates results for compound 1) inhibiting the growth of MCF-7 breast cancer cells.

[Key to FIG. 1:]
Zellproliferation (% der Kontrolle mit E2)=Cell proliferation (% of the control with E2)
Kontrolle [ohne E2]=Control [without E2 ]
Kontrolle [mit 10—10 M E2]=Control [ with 10—10 M E2]
Verbindung 1=Compound 1
Konzentration =Concentration Pharmaceutical Preparations and Indications The compounds of general formula II represent compounds with antiestrogenic action after peroral or parenteral administration.

Moreover, the compounds according to the invention are pure antiestrogens.

This invention comprises the novel substances as pharmaceutical active ingredients, their production, their therapeutic application and the pharmaceutical dispensing forms that contain the new substances. The chemical compounds are new steroidal ERα-selective antagonists.

The new selective ERα antagonists that are described in this patent can be used as individual components or in combination in particular with estrogens or antigestagens in pharmaceutical preparations. The novel selective ERα antagonists are suitable both for treating estrogen-dependent diseases, such as, for example, endometriosis; breast cancers, endometrial carcinomas, and antiovulatory infertility, and for treating prostate cancers, prostate hyperplasias, and melanomas as well as lung cancers.

The compounds of general formula II can be used as components in the products that are described in EP 346014 B1 that contain an estrogen and a pure antiestrogen, namely for simultaneous, sequential or separate use for the selective estrogen therapy of perimenopausal or postmenopausal women.

The compounds of general formula II can be used together with antigestagens (competitive progesterone antagonists) for treating hormone-dependent tumors (EP 310 542 A).

Other indications in which the compounds of general formula II can be used are male hair loss, a diffuse alopecia, an alopecia that is caused by chemotherapy as well as hirsutism (H.-S. Oh, R. C. Smart, Proc. Natl. Acad. Sci. USA, 93, 1996, 12525–12530).

The compounds of general formula II can also be used for the production of pharmaceutical compositions for male and female birth control.

The compounds of general formula II according to the invention and their acid addition salts are suitable for the production of pharmaceutical compositions and preparations. The pharmaceutical compositions or pharmaceutical agents contain as active ingredient at least one or more of the compounds of general formula II according to the invention or their acid addition salts, optionally in combination with other pharmacologically active substances or pharmaceutical adjuvants. The production of the pharmaceutical agents is carried out in a known way, whereby the known and commonly used pharmaceutical adjuvants as well as other commonly used vehicles and diluents can be used.

As such vehicles and adjuvants, for example, those are suitable that are recommended or indicated in the following bibliographic references as adjuvants for pharmaceutics, cosmetics and related fields: Ullmann's Enzyklopädie der technischen Chemie [Ullmann's Encyclopedia of Technical Chemistry], 4, 1953, 1–39; J. Pharm. Sciences, 52, 1963, 918 ff; issued by Czetsch-Lindenwald, Hilfsstoffe für Pharmazie und angrenzende Gebiete [Adjuvants for Pharmaceutics and Related Fields]; Pharm. Ind. 2, 1961, 72 ff; Dr. H. P. Fiedler, Lexikon der Hilfsstoffe für Pharmazie, Kosmetik und angrenzende Gebiete [Dictionary of Adjuvants for Pharmaceutics, Cosmetics and Related Fields], Cantor KG, Aulendorf in Württemberg 1971.

The compounds of general formula II according to the invention can be administered orally or parenterally, e.g., intraperitoneally, intramuscularly, subcutaneously and percutaneously. The compounds can also be implanted in the tissue.

Dosage

The amount of the compounds to be administered fluctuates within a wide range and can cover any effective amount. Based on the condition to be treated and the type of administration, the amount of the administered compound can be 0.1–25 mg/kg of body weight, preferably 0.5-5 mg/kg of body weight. In humans, this corresponds to a daily dose of 5 to 1250 mg. The preferred daily dosage in humans is 50 to 200 mg.

For oral administrations, tablets, film tablets, coated tablets, capsules, pills, powder, solutions or suspensions or else depot forms are suitable. Suitable tablets can be obtained, for example, by mixing active ingredient with known adjuvants, for example inert diluents such as dextrose, sugar, sorbitol, mannitol, polyvinyl pyrrolidone, explosives such as corn starch or alginic acid, binders such as starch or gelatin, lubricants such as magnesium stearate or talc and/or agents for achieving a depot effect such as carboxyl polymethylene, carboxylmethyl cellulose, cellulose acetate phthalate or polyvinyl acetate. The tablets can also consist of several layers.

Correspondingly, coated tablets can be produced by coating cores that are produced analogously to the tablets with agents that are commonly used in tablet coatings, for example polyvinyl pyrrolidone or shellac, gum arabic, talc, titanium oxide or sugar. In this case, the coated tablet shell can also consist of several layers, whereby the adjuvants that are mentioned above in the tablets can be used.

Solutions or suspensions with the compounds of general formula II according to the invention can in addition contain taste-improving agents such as saccharine, cyclamate or sugar as well as, e.g., flavoring substances such as vanilla or orange extract. In addition, they can contain suspension adjuvants such as sodium carboxymethyl cellulose or preservatives such as p-hydroxybenzoates.

The compounds of general formula II that contain capsules can be produced, for example, by the compound of general formula II being mixed with an inert vehicle such as lactose or sorbitol and encapsulated in gelatin capsules.

To achieve a better bioavailability of the active ingredient, the compounds of general formula II can also be formulated as cyclodextrin clathrates. To this end, the compounds are reacted with α-, β- or γ-cyclodextrin or derivatives of the latter (PCT/EP 95/02656).

For parenteral administration, the active ingredients can be dissolved or suspended in a physiologically compatible diluent. As diluents, very often oils with or without the addition of a solubilizer, a surfactant, a suspending agent or emulsifying agent are used. Examples of oils that are used are olive oil, peanut oil, cottonseed oil, soybean oil, castor oil and sesame oil.

The compounds of general formula II can also be formulated in the form of a solution that is intended for oral administration and that in addition to the active compound of general formula II contains a) a pharmaceutically compatible oil and/or b) a pharmaceutically compatible lipophilic surfactant and/or c) a pharmaceutically compatible hydrophilic surfactant and/or d) a pharmaceutically compatible water-miscible solvent.

To this end, reference is made in addition to WO 97/21440.

The compounds can also be used in the form of a depot injection or an implant preparation that can be formulated in such a way that a delayed release of the active ingredient is made possible.

Implants can contain as inert materials, for example, biodegradable polymers, or synthetic silicones such as, for example, rubber gum. In addition, the active ingredients can be added, for example, to a patch for percutaneous administration.

For the production of intravaginal systems (e.g., vaginal rings) or intrauterine systems (e.g., pessaries, coils) that are loaded with active compounds of general formula II, various polymers, such as, for example, silicone polymers, ethylene vinyl acetate, polyethylene or polypropylene, are suitable.

The compounds of general formula II according to the invention can be produced as described below.

The production of 11β-substituted 19-nor-17α-pregna-1, 3,5(10)-trien-17β-ols with a 21,16α-lactone ring can be carried out in a one-stage process from the corresponding 17-oxo compounds or the 17α-cyanomethylated estra-1,3,5 (10)-triene derivatives (non-prepublished DE 100 48 634). The formation of the iminoether and thus also the lactone is connected to the presence of a 17α-cyanomethyl substituent.

Starting substances for the synthesis of the 11β-alkyl-substituted 17β-hydroxy-19-nor-17α-pregna-1,3,5(10)-triene-21,16α-lactones are compounds of general formula III

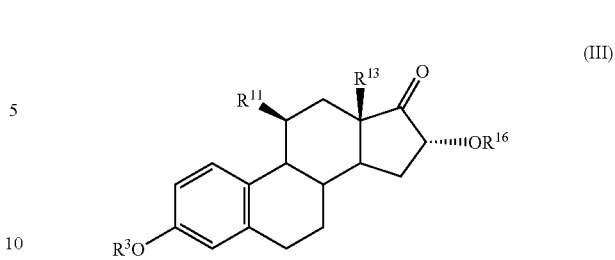

in which

R$^3$ means a C$_{1-4}$-alkyl, C$_{2-6}$-acyl or tri(C$_{1-4}$-alkyl)silyl group, R$^{11}$ means a straight-chain alkyl radical with 6 to 17 carbon atoms, R$^{13}$ means a methyl or ethyl group, R$^{16}$ means an acetyl or trimethylsilyl group.

The 11β-alkyl substitution is carried out by regioselective and stereoselective syntheses as described in the literature. The electrophilic estradiol derivative, for example the 5α, 10α-epoxy-estr-9(11)ene derivative, is produced from an estra-5(10),9(11)-dien-17β-ol that is protected in 3-position (Teutsch et al. U.S. Pat. No. 4,447,424; Faraj et al. J. Chem. Soc., Perkin Trans 1, 1990, 3045–3048). Reaction with Grignard reagents R$^{11}$MgX (X=halogen, such as bromine, chlorine) in the presence of catalytic amounts of copper(I)-chloride results in the 11β-alkyl-substituted 5α-hydroxy-9 (10)ene derivative (Belanger et al., Steroids 37, 1981, 361–382). Carried out simultaneously with the addition of acids are the deketalization and dehydration of the 11β-alkyl-substituted compound that is used in a subsequent isomerization reaction with hydrogen with the addition of a catalyst. The thus obtained 11β-alkyl-substituted estra-1,3, 5(10)-trien-17-one derivative is protected in 3-position and then converted in the usual way to a 16α-bromine compound. Compounds of general formula II are obtained by alkaline hydrolysis and protection of the 16α-hydroxy function that is obtained.

As an alternative to this, the introduction of the 16-hydroxy function can be performed by reaction of 17-silyl- or 17-acylenol ethers with peracids and subsequent hydrolysis.

By reaction of the compounds of general formula III with lithium acetonitrile that is produced in situ, a 17α-cyanomethyl-16α-hydroxylate is produced at an intermediate stage. By the addition of the 16α-alcoholate to the nitrile group and subsequent hydrolysis of the iminoether that is formed, the lactone is formed.

By the use of compounds according to general formula III, in which R$^{16}$ means trimethylsilyl or acetyl, a portion of about 60% of 17α-cyanomethylated product can be reacted in situ in a one-pot process to form 21,16α-lactone.

The saponification of ester groupings as well as etherification and/or esterification of free hydroxyl groups is carried out in each case according to established processes of organic chemistry.

The sulfamates according to the invention are accessible in a way that is known in the art from the corresponding hydroxy steroids by esterification with sulfamoyl chlorides in the presence of a base (Z. Chem. 15, 270–272 (1975); Steroids 61, 710–717 (1996)).

Subsequent acylation of the sulfamide group results in the (N-acyl)sulfamates according to the invention (cf. DE 195 40 233 A1).

The acid addition salts of the compounds of general formula II can also be produced according to standard processes from the free acids of the compounds of general formula II.

The following examples are used for a more detailed explanation of the invention, without being limited thereto:

General Production Process 8 ml (20 mmol) of n-butyllithium solution (2.5 M in toluene) is cooled to −25° C. to −35° C. while being stirred in a reaction vessel that was rendered inert. Then, the solution is diluted by adding 8 ml of tetrahydrofuran while being cooled and reacted with 1.15 ml (22 mmol) of acetonitrile in the above-mentioned temperature range. A white to yellowish suspension of lithium acetonitrile is produced.

A solution of 2.5 mmol of the steroid of general formula III (e.g., 1.14 g of 11β-hexyl-17-oxo-estra-1,3,5(10)-triene-3,16α-diyl-diacetate) in 8 ml of tetrahydrofuran is added to this suspension while the reaction temperature is kept from −25° C. to −35° C.

After one hour of reaction time in the above-mentioned temperature range, the batch is mixed with water, neutralized with dilute hydrochloric acid, the tetrahydrofuran is distilled off, and the crude product mixture is isolated by extraction with ethyl acetate.

By chromatography on silica gel 60 with an eluant mixture of chloroform/n-hexane/methanol (45/45/10), the product can be separated and isolated.

EXAMPLE 1

546 mg (53% of theory) of 3,17β-dihydroxy-11β-hexyl-19-nor-17α-pregna-1,3,5(10)-triene-21,16α-lactone is obtained from 2.5 mmol (1.14 g) of 11β-hexyl-17-oxo-estra-1,3,5(10)-triene-3,16α-diyl-diacetate.

In addition, the following compounds are obtained analogously:

3,17β-Dihydroxy-11β-octyl-19-nor-17α-pregna-1,3,5(10)-triene-21,16α-lactone
3,17β-Dihydroxy-11β-decyl-19-nor-17α-pregna-1,3,5(10)-triene-21,16α-lactone
3,17β-Dihydroxy-11β-dodecyl-19-nor-17α-pregna-1,3,5(10)-triene-21,16α-lactone Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosure[s] of all applications, patents and publications, cited herein and of corresponding German Patent Application No. 102 14180.0, filed Mar. 27, 2002, and U.S. Provisional Application Ser. No. 60/374,516, filed Apr. 23, 2002 are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A 19-Nor-17α-pregna-1,3,5(10)-triene with a 21,16α-lactone ring of formula (II)

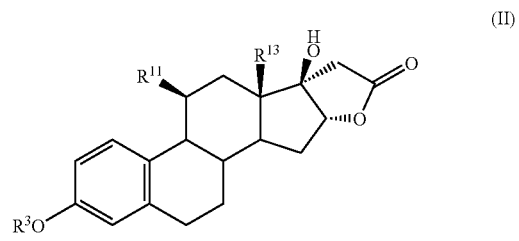

in which
R$^3$ is a hydrogen atom, a C$_{1-4}$-alkyl, C$_{2-6}$-acyl, a tri(C$_{1-4}$-alkyl)silyl group or R$^{18}$SO$_2$-,
R$^{18}$ is R$^{19}$R$^{20}$N-,
R$^{19}$ and R$^{20}$ are, independently of one another, a hydrogen atom, a C$_{1-5}$-alkyl radical, or C(O)R$^{21}$,
R$^{21}$ is a straight-chain or branched hydrocarbon radical with up to 6 carbon atoms, a C$_{3-7}$-cycloalkyl radical, an aryl radical, an aralkyl radical or an alkylaryl radical,
R$^{11}$ is a straight-chain alkyl radical with 6 to 17 carbon atoms, and
R$^{13}$ is a methyl or ethyl groups,
or a pharmaceutically acceptable salt thereof.

2. A 19-Nor-17α-pregna-1,3,5(10)-triene with a 21,16α-lactone ring or a pharmaceutically acceptable salt thereof according to claim 1, in which R$^{11}$ is hexyl, octyl, decyl or dodecyl.

3. A 19-Nor-17α-pregna-1,3,5(10)-triene with a 21,16α-lactone ring or a pharmaceutically acceptable salt thereof according to claim 1, in which R$^3$ is a hydrogen atom.

4. A 19-Nor-17α-pregna-1,3,5(10)-triene with a 21,16α-lactone ring according to claim 1, which is 3,17β-Dihydroxy-11β-hexyl-19-nor-17α-pregna-1,3,5(10)-triene-21,16α-lactone,
3,17β-Dihydroxy-11β-octyl-19-nor-17α-pregna-1,3,5(10)-triene-2 1,1 6-lactone,
3,17β-Dihydroxy-11β-decyl-19-nor-17α-pregna-1,3,5(10)-triene-2 1,1 6-lactone, or
3,17β-Dihydroxy-11β-dodecyl-19-nor-17α-pregna-1,3,5(10)-triene-2 1,16α-lactone1 or a pharmaceutically acceptable salt thereof.

5. A 19-Nor-17α-pregna-1,3,5(10)-triene with a 21,16α-lactone ring or a pharmaceutically acceptable salt thereof according to claim 1, in which R$^3$ means a methyl group.

6. A 19-Nor-17α-pregna-1,3,5(10)-triene with a 21,16α-lactone ring or a pharmaceutically acceptable salt thereof according to claim 1, in which R$^{13}$ means a methyl group.

7. A 19-Nor-17α-pregna-1,3,5(10)-triene with a 21,≠α-lactone ring or a pharmaceutically acceptable salt thereof according to claim 1, in which R$^3$ means a hydrogen atom or a methyl group, means a methyl group, and R$^{11}$ is hexyl, octyl, decyl or dodecyl.

8. A pharmaceutical composition comprising at least one compound of formula II or a pharmaceutically acceptable salt thereof according to claim 1 and a pharmaceutically compatible vehicle.

9. A pharmaceutical composition comprising at least one compound of formula II or a pharmaceutically acceptable salt thereof according to claim 4 and a pharmaceutically compatible vehicle.

10. A pharmaceutical composition comprising at least one compound of formula II or a pharmaceutically acceptable salt thereof according to claim 2 and a pharmaceutically compatible vehicle.

11. A pharmaceutical composition comprising at least one compound of formula II or a pharmaceutically acceptable salt thereof according to claim 7 and a pharmaceutically compatible vehicle.

12. A pharmaceutical composition comprising at least one compound of formula II or a pharmaceutically acceptable salt thereof according to claim 3 and a pharmaceutically compatible vehicle.

13. A pharmaceutical composition comprising at least one compound of formula II or a pharmaceutically acceptable salt thereof according to claim 5 and a pharmaceutically compatible vehicle.

14. A method for treating breast cancer, endometrial carcinoma or prostate cancer comprising administering to a patient in need thereof an effective amount of a pharmaceutical composition according to claim 8.

15. A method for treating breast cancer, endometrial carcinoma or prostate cancer comprising administering to a patient in need thereof an effective amount of a pharmaceutical composition according to claim 9.

16. A method for treating breast cancer, endometrial carcinoma or prostate cancer comprising administering to a patient in need thereof an effective amount of a pharmaceutical composition according to claim 10.

17. A method for treating breast cancer, endometrial carcinoma or prostate cancer comprising administering to a patient in need thereof an effective amount of a pharmaceutical composition according to claim 11.

18. A method for treating breast cancer, endometrial carcinoma or prostate cancer comprising administering to a patient in need thereof an effective amount of a pharmaceutical composition according to claim 12.

19. A method for treating breast cancer, endometrial carcinoma or prostate cancer comprising administering to a patient in need thereof an effective amount of a pharmaceutical composition according to claim 13.

20. A method for selectively antagonizing an alpha estrogen receptor comprising selectively antagonizing said alpha estrogen receptor with a 19-Nor-17$\alpha$-pregna-3,5(10)-triene with a 21,$\neq\alpha$-lactone ring or a pharmaceutically acceptable salt thereof according to claim 1.

* * * * *

UNITED STATES PATENT AND TRADEMARK OFFICE
CERTIFICATE OF CORRECTION

PATENT NO. : 7,119,082 B2 Page 1 of 1
APPLICATION NO. : 10/397854
DATED : October 10, 2006
INVENTOR(S) : Gerd Mueller It is certified that error appears in the above-identified patent and that said Letters Patent is hereby corrected as shown below:

Column 14, line 42, reads "(10)-triene-2 1,1 6-lactone," should read -- (10)-triene-21, 16α-lactone, --
Column 14, line 44, reads "(10)-triene-2 1,1 6-lactone, or" should read -- (10)-triene-21, 16α-lactone, or --
Column 14, line 46, reads "(10)-triene-2 1,16α -lactonel or" should read -- (10)-triene-21,16α-lactone, or --
Column 14, line 55, reads "21,≠α" should read -- 21,16α --
Column 14, line 58, reads "group, means" should read -- group, $R^{13}$ means --
Column 16, line 20, reads "3,5(10)-triene" should read -- 1,3,5(10)-triene --
Column 16, line 21, reads "21,≠α" should read -- 21,16α --

Signed and Sealed this

Twentieth Day of March, 2007

JON W. DUDAS
*Director of the United States Patent and Trademark Office*